(12) United States Patent
Ko

(10) Patent No.: US 10,194,987 B2
(45) Date of Patent: Feb. 5, 2019

(54) LASER IRRADIATION APPARATUS AND LASER IRRADIATION METHOD

(71) Applicant: LUTRONIC CORPORATION, Goyang (KR)

(72) Inventor: Kwang Chon Ko, Paju (KR)

(73) Assignee: LUTRONIC CORPORATION, Goyang (KR)

( * ) Notice: Subject to any disclaimer, the term of this patent is extended or adjusted under 35 U.S.C. 154(b) by 173 days.

(21) Appl. No.: 14/778,044

(22) PCT Filed: Mar. 19, 2014

(86) PCT No.: PCT/KR2014/002307
§ 371 (c)(1),
(2) Date: Sep. 17, 2015

(87) PCT Pub. No.: WO2014/148814
PCT Pub. Date: Sep. 25, 2014

(65) Prior Publication Data
US 2016/0278862 A1    Sep. 29, 2016

(30) Foreign Application Priority Data

Mar. 19, 2013  (KR) .................. 10-2013-0029354

(51) Int. Cl.
*A61B 18/24*    (2006.01)
*A61B 18/00*    (2006.01)
(Continued)

(52) U.S. Cl.
CPC .... *A61B 18/24* (2013.01); *A61B 2018/00339* (2013.01); *A61B 2018/2238* (2013.01);
(Continued)

(58) Field of Classification Search
CPC ............. A61B 18/24; A61B 2090/376; A61B 2018/00339; A61B 2018/2238; A61B 2018/2272; A61B 2218/002; A61B 18/245
(Continued)

(56) References Cited

U.S. PATENT DOCUMENTS 5,537,499 A * 7/1996 Brekke .................. A61B 18/24
385/123
5,713,913 A * 2/1998 Lary .............. A61B 17/320725
604/103.1
(Continued)

FOREIGN PATENT DOCUMENTS

JP    07-080086 A    3/1995
JP    2007-117189 A  5/2007
JP    2008-194455 A  8/2008

OTHER PUBLICATIONS

International Search Report for PCT/KR2014/002307 filed on Mar. 19, 2014.

*Primary Examiner* — Gary Jackson
*Assistant Examiner* — Zahed Kabir

(57) ABSTRACT

The present invention relates to a laser irradiation apparatus and a laser irradiation method. The laser irradiation apparatus, according to the present invention, comprises: an optical fiber which transmits a laser and has a light emitting surface; a protecting member for covering an end portion of the optical fiber including the light emitting surface; and an indication member which is identified by an X-ray and indicates the position and/or direction of the light emitting surface.

4 Claims, 10 Drawing Sheets

(51) Int. Cl.
*A61B 18/22* (2006.01)
*A61B 90/00* (2016.01)

(52) U.S. Cl.
CPC . *A61B 2018/2272* (2013.01); *A61B 2090/376* (2016.02); *A61B 2218/002* (2013.01)

(58) Field of Classification Search
USPC .......................................... 606/14; 604/516
See application file for complete search history.

(56) References Cited

U.S. PATENT DOCUMENTS

| | | | | |
|---|---|---|---|---|
| 6,493,575 | B1* | 12/2002 | Kesten | A61B 90/36 600/431 |
| 2010/0030190 | A1* | 2/2010 | Singh | A61F 7/123 604/516 |
| 2011/0224538 | A1* | 9/2011 | Linares | A61B 8/0841 600/424 |
| 2011/0306956 | A1* | 12/2011 | Islam | A61B 18/20 606/15 |
| 2012/0004529 | A1* | 1/2012 | Tolkowsky | A61B 6/12 600/407 |
| 2013/0051728 | A1 | 2/2013 | Petroff et al. | |
| 2014/0222093 | A1* | 8/2014 | Mafi | A61B 17/8855 606/86 R |
| 2015/0045675 | A1* | 2/2015 | Chernomorsky | A61B 18/1477 600/471 |

\* cited by examiner

Expected irradiation region

LASER IRRADIATION APPARATUS AND LASER IRRADIATION METHOD

BACKGROUND OF THE INVENTION

Field of the Invention

The present invention relates to a laser irradiation apparatus which has a side firing function and capable of confirming irradiation information and a laser irradiation method using the same.

Related Art

Since treatment using a laser allows incision, removal, and suture of a bodily tissue without through surgical operation, healing is possible within a short time with a small curing cost. Accordingly, in recent years, the range of curing using the laser is extending to dermatology, an orthopedics, and a plastic surgery as well as a surgery The treatment using the laser generally inputs a laser (for example, Nd:YAG laser) toward a bodily tissue. The laser is absorbed in a corresponding bodily tissue so that the corresponding bodily tissue emit heat to use a time period when the corresponding bodily tissue is cut, removed, sewed, and modified.

The above laser is transmitted using an optical fiber and is irradiated to an outside from an end portion of the optical fiber. In some cases, there is a need to irradiate the laser in a side direction of a longitudinal direction of the optical fiber. Such side irradiation refers to side firing. However, when the side firing scheme is used in an inside of the body, it is difficult to confirm irradiation information on from where the laser is irradiated to a certain direction.

SUMMARY OF THE INVENTION

The present invention provides a laser irradiation apparatus capable of easily confirming irradiation information and a laser irradiation method using the same.

In order to accomplish the above object, in accordance with an aspect of the present invention, there is provided a laser irradiation apparatus including: an optical fiber which transmits a laser and has a light emitting surface; a protecting member for covering an end portion of the optical fiber including the light emitting surface; and an indication member which is identified by an X-ray and indicates a position and a direction of the light emitting surface.

The light emitting surface may be inclined and cut for lateral irradiation.

The indication member may be located in at least one of an inside and a surface of the protecting member.

The indication member may include at least one of: a front indication member located in a front portion of the light emitting surface when viewed in a longitudinal direction of the optical fiber and a lateral indication member located in a lateral side of the optical fiber.

The indication member may include the front indication member, and the front indication member has a shape having directionality.

The laser irradiation apparatus of claim 4, wherein the indication member comprises the lateral indication member, and the lateral indication member has a shape having directionality.

In accordance with another aspect of the present invention, there is provided a laser irradiation method including: arranging an optical fiber including a light emitting surface close to an irradiation target; confirming an irradiation position and an irradiation direction of a laser to be irradiated to the light emitting surface using an indication member which is identified by an X-ray and indicates a position and a direction of the light emitting surface; and irradiating the laser after confirming the irradiation position and the irradiation direction of the laser.

The light emitting surface may be inclined and cut for lateral irradiation.

The indication member may be located in at least one of an inside and a surface of the protecting member.

The indication member may include at least one of: a front indication member located in a front portion of the light emitting surface when viewed in a longitudinal direction of the optical fiber and a lateral indication member located in a lateral side of the optical fiber.

The indication member may include the front indication member, and the front indication member has a shape having directionality.

The indication member may include the lateral indication member, and the lateral indication member has a shape having directionality.

Advantageous Effects

In accordance with the present invention, a laser irradiation apparatus capable of easily confirming irradiation information and a laser irradiation method using the same are provided.

DESCRIPTION OF EXEMPLARY EMBODIMENTS

Hereinafter, a curing method according to an exemplary embodiment of the present invention will be described with reference to the accompanying drawings. In the following description, a location relationship between constituent elements will be principally described based on drawings. The drawings may be exaggerated, omitted or schematically drawn for the purpose of convenience or clarity. Accordingly, the present invention is not limited thereto. Various variations and modifications are possible in the component parts and/or arrangements of the subject combination arrangement within the scope of the disclosure.

As one example, a side firing scheme will be described in a following embodiment. However, the present invention is not limited thereto. The side firing scheme may be used to confirm an irradiation position and/or an irradiation direction of the laser. Further, the side firing scheme is not limited to a configuration to inclined-cut an end portion of an optical fiber, but the present invention is applicable to other side firing schemes using a reflective surface.

The laser irradiation apparatus according to according to a first embodiment of the present invention will be described with reference to FIG. 1 to FIG. 4.

Figure 1:
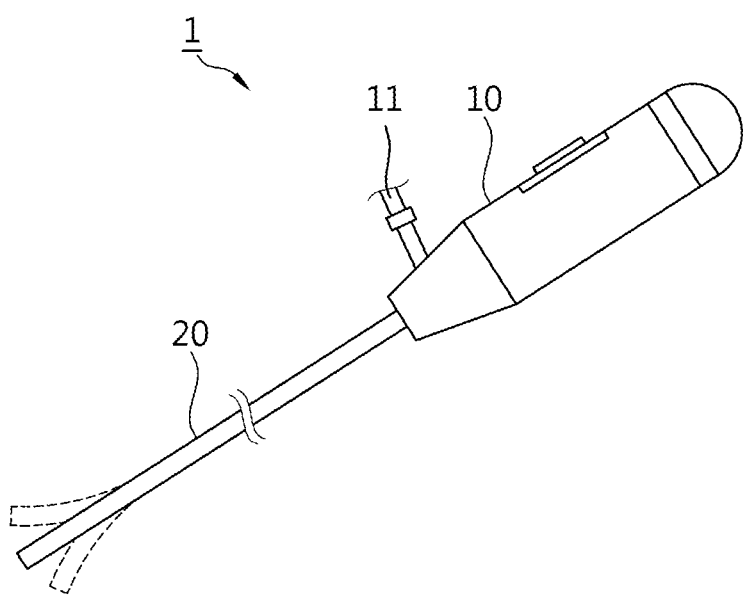
FIG. 1 illustrates a laser irradiation apparatus according to a first embodiment of the present invention.
Figure 2:
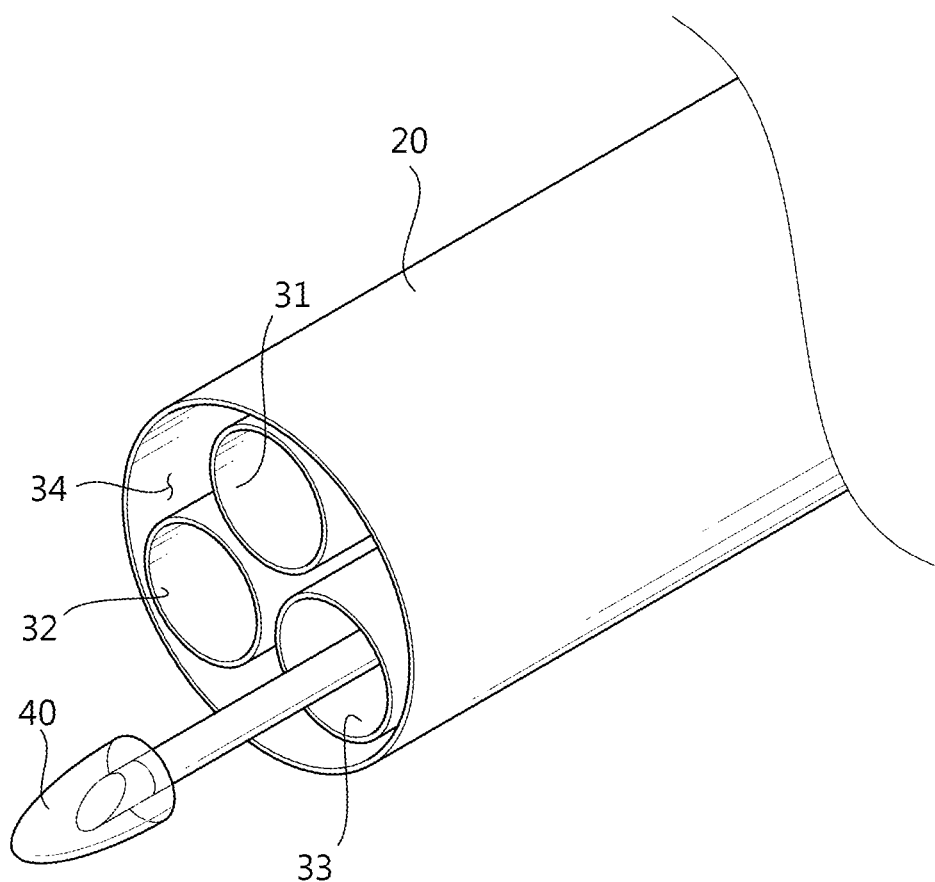
FIG. 2 is an enlarged view illustrating a main portion of the laser irradiation apparatus according to a first embodiment of the present invention.
Figure 3:
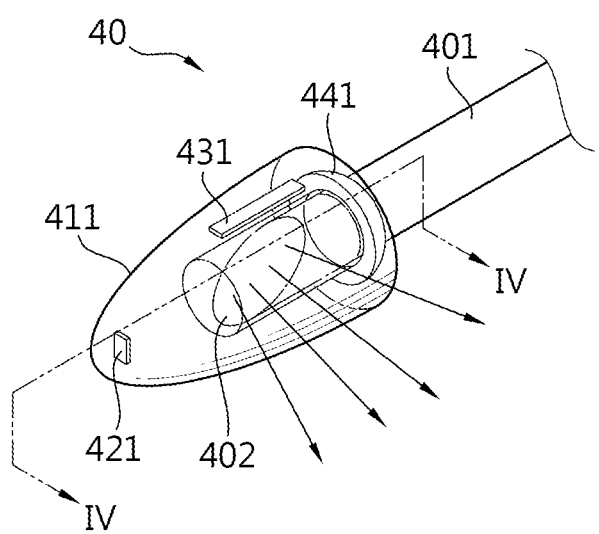
FIG. 3 is a perspective view illustrating a laser assembly according to a first embodiment of the present invention.
Figure 4:
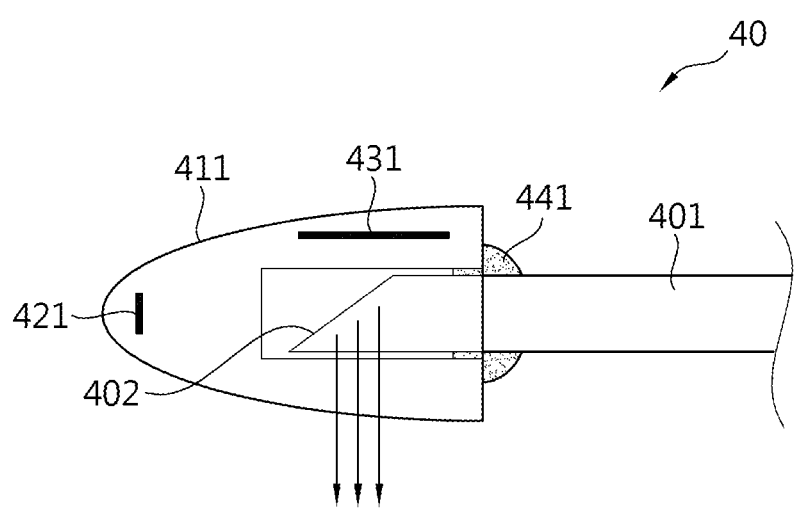
FIG. 4 is a sectional view taken along line IV-IV of FIG. 3.

FIG. 1 illustrates a laser irradiation apparatus according to a first embodiment of the present invention, FIG. 2 is an enlarged view illustrating a main portion of the laser irradiation apparatus according to a first embodiment of the present invention, FIG. 3 is a perspective view illustrating a laser assembly according to a first embodiment of the present invention, and FIG. 4 is a sectional view taken along line IV-IV of FIG. 3.

The laser irradiation apparatus 1 includes a hand piece 10, a catheter 20, and a laser assembly 40. A plurality of channels 31, 32, and 33 are formed at an end portion of the catheter 20. The laser assembly 40 includes an optical fiber 401, a protecting member 411, indication members 421 and 431, and a coupling member 441.

A channel port 11 is formed in the hand piece 10. The laser assembly 40 is inserted into the channel port 11. The laser assembly 40 inserted into the channel port 11 is expose to an outside of the end portion of the catheter 20 through the channel 30 which is formed at the catheter 20. The laser assembly 40 receives a laser from a laser supply device (not shown) to irradiate the laser from the end portion of the optical fiber 401. A plurality of channel ports 11 may be provided, and may be used for insertion of an optical fiber for photographing.

The catheter 20 has a long extension shape and the channels 31, 32, and 33 are formed through a full length of the catheter 20. The optical fiber (not shown) for photographing and a treatment device (not shown) may be inserted and drugs may be provided through channels 31 and 32 except for the channel 33 which is used for insertion of the laser assembly 40. Moreover, foreign materials after the treatment may be discharged through the channels 31, 32, and 33. Water may circulate through the channels 31, 32, and 33. Illumination may be provided through a space 34 of the catheter 20 except for the channels 31, 32, and 33. Although not shown, a steering wire is provided at the catheter 20 and may adjust a direction of the catheter 20.

A light emitting surface 402 of the end portion of the optical fiber 410 is inclined and cut. The laser transmitted through the optical fiber is reflected from the light emitting surface and is irradiated in a lateral direction. The protecting member 411 covers the end portion of the optical fiber 401. The protecting member 411 may be made by a material which does not exert an influence on the irradiated laser. For example, the protecting member 411 may be made by glass or a transparent plastic material.

The protecting member 411 prevents the sharp end portion of the optical fiber 410 due to the light emitting surface 402 from being broken or a human body from being hurt.

The protecting member 411 has a thimble shape and is fixed to the optical fiber 401 through a bonding member 411.

The indication members 421 and 431 are located inside the protecting member 411. The indication members 421 and 431 include a front indication member 421 located in a front portion of the light emitting surface when viewed in a longitudinal direction of the optical fiber and a lateral indication member located around the end portion of the optical fiber 401.

The indication members 421 and 431 are provided by a metal component detected by X-ray. The indication members 421 and 431 have a long metal pole shape. The lateral indication member 331 is longer than the front indication member 421.

When an inside of the human body is treated using the laser, it is difficult to confirm a location to which the laser is irradiated. When the end portion of the optical fiber is located away from the catheter 20, it is more difficult to confirm the location of the laser. In addition, in a case of the side firing structure, it is also difficult to confirm a direction to which the laser is irradiated. When the laser is irradiated to a region different from a treatment target, since great adverse reaction is produced in a patient, it is very important to confirm the irradiation position and direction of the laser.

The above laser irradiation laser 1 according to the first embodiment may easily confirm the irradiation position and direction of the laser. The laser assembly for photographing the irradiation position and direction of the laser by X-ray will be described with reference to FIG. 5. Hereinafter, the laser assembly represents a configuration of an end portion of the optical fiber to which the laser is irradiated and is distinguished from an optical fiber except for the end portion.

When the optical fiber 401 is pushed through the channel port 11 during a treatment procedure, the laser assembly 40 protrudes from the end portion of the catheter 20. Accordingly, a photographing device (not shown) provided at the channels 31 and 32 cannot confirm the irradiation position and the irradiation direction of the laser assembly 40. In addition, even if the laser assembly 40 is located close to the end portion of the catheter 20, it is not easy to confirm the irradiation direction of the laser.

Figure 5:
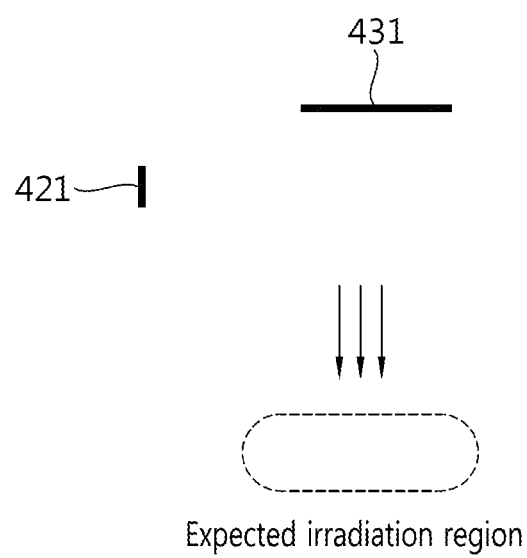
FIG. 5 illustrates an X-ray photographing result and an expected irradiation region of the laser irradiation apparatus according to a first embodiment of the present invention.

According to the present invention, the irradiation position and the irradiation direction of the laser may be easily and exactly confirmed by X-ray photographing. If the X-ray photographing is performed, as shown in FIG. 5, the front indication member 421 and the lateral indication member 431 are photographed. Since the lateral indication member 431 is longer than the front indication member 421, the position and the direction of the light emitting surface may be confirmed from a position relation between the lateral indication member 431 and the front indication member 421. Accordingly, an expected irradiation region in a current position of the laser assembly may be known.

When the expected irradiation region corresponds to a treatment region, the treatment starts by irradiating the laser. The X-ray photographing is continuously performed during laser irradiation to confirm whether the irradiation region corresponds to the treatment region. If the expected irradiation region deviates from the treatment region during the irradiation procedure, the laser irradiation stops or the laser is irradiated by adjusting the arrangement of the laser assembly 40 so that the irradiation region corresponds to the treatment region.

An irradiation method using the laser irradiation apparatus according to the present invention will be described with reference to FIG. 6 to FIG. 8. In a following description, although a method of irradiating a laser on a disc herniation surface using the laser irradiation apparatus will be described, the present invention is not limited thereto but is applicable to all laser irradiation methods performed inside the human body.

An intervertebral disc is located between spine bones to flexibly and firmly maintain a connection state of the spine bones. The intervertebral disc refers to a spinal disc. The intervertebral disc includes a center nucleus pulposus and an anulus fibrosus surrounding the center nucleus pulposus. When an unnecessary nerve is grown on a surface of the anulus fibrosus, a pain occurs. In this case, the unnecessary nerve may be removed by irradiating the laser on the surface of the anulus fibrosus.

Figure 6:
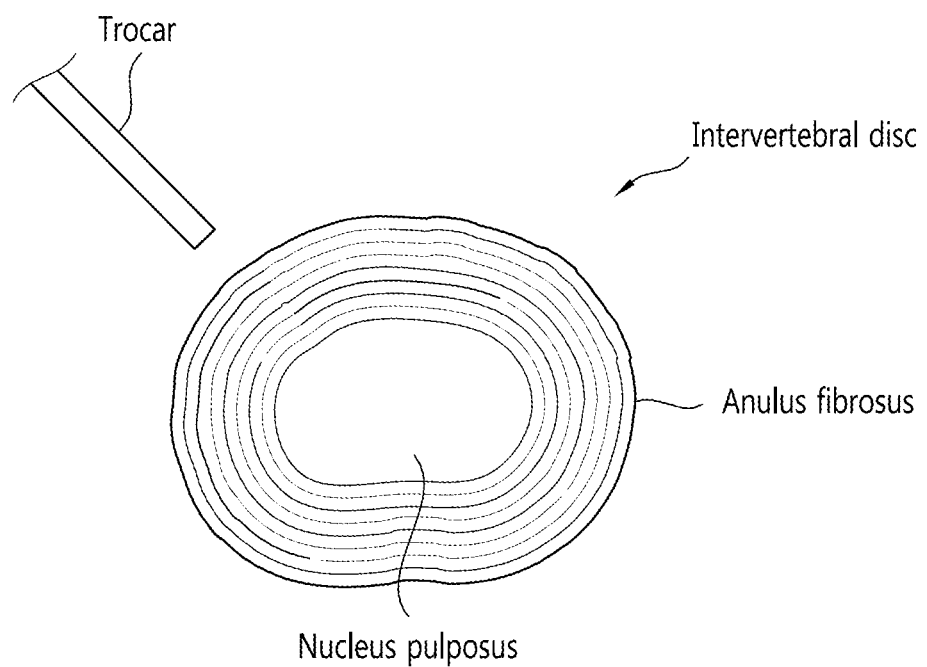
FIG. 6 to FIG. 8 are views illustrating a laser irradiation method using the laser irradiation apparatus according to a first embodiment of the present invention.

First, as shown in FIG. 6, a trocar is invaded in an inclined direction from a shoulder of a patient. A surgical operation method using the trocar refers to a minimally invasive surgery.

Figure 7:
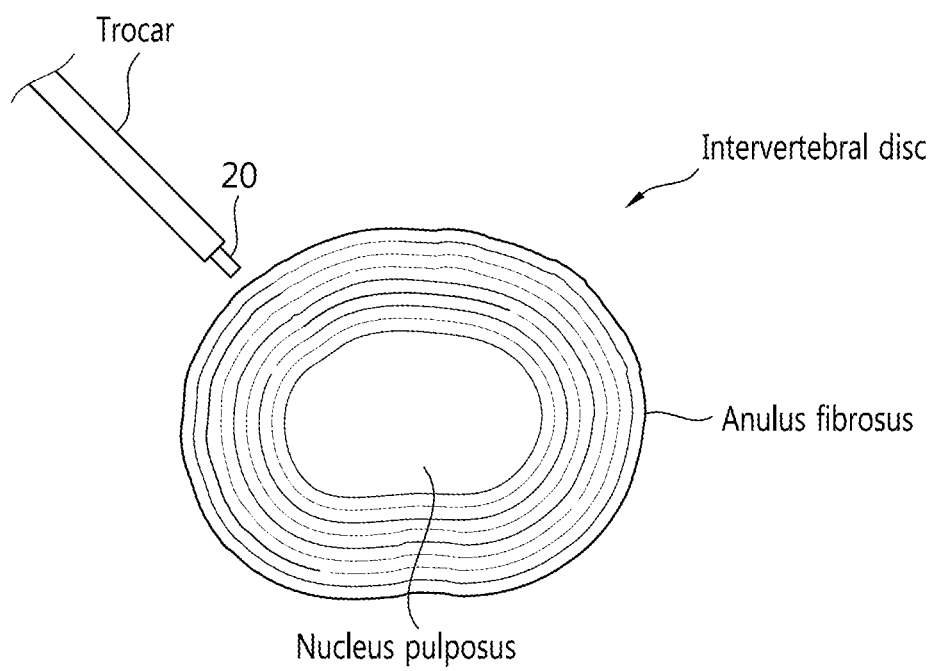

Next, as shown in FIG. 7, the catheter 20 is introduced through the trocar. In this state, an operator may confirm a state of the surface of the anulus fibrosus through a photographing device.

Figure 8:
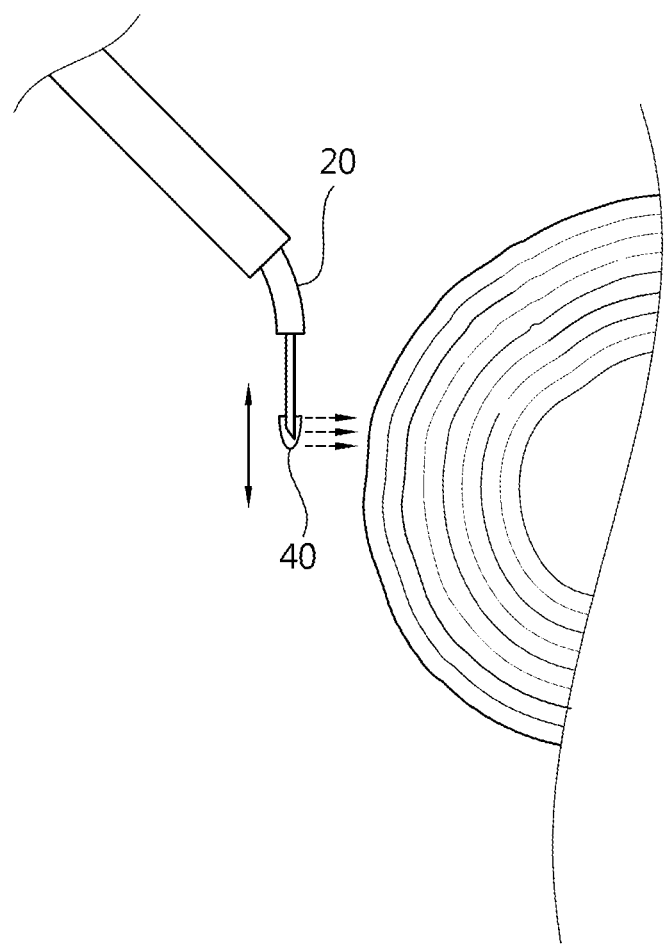

Next, as shown in FIG. 8, the catheter 20 is bent using the steering wire so that the catheter 20 is located with the surface of the anulus fibrosus in parallel and the laser assembly 40 extends to a position to which the laser is irradiated. During the procedure, the position and arrangement of the indication members 421 and 431 are confirmed by irradiating X-ray. The irradiation position and direction of the laser are confirmed from the position of arrangement of the indication members 421 and 431. When the expected irradiation region is the surface of the anulus fibrosus being the treatment target, the laser is irradiated.

The laser is irradiated on the surface of the anulus fibrosus by moving the laser assembly 40 along the surface of the anulus fibrosus. During the above procedure, if the indication members 421 and 431 are photographed continuously or at a predetermined interval through X-ray, the laser is not irradiated to a region which is not expected and the treatment may be stably performed.

During the treatment procedure, a drug solution may be injected or water may circulate through other channels 31 and 32.

Figure 9:
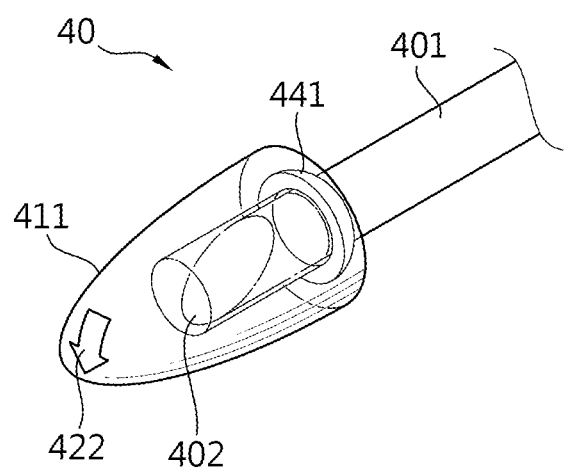
FIG. 9 is a perspective view illustrating a laser assembly according to a second embodiment of the present invention.

FIG. 9 is a perspective view illustrating a laser assembly according to a second embodiment of the present invention.

As illustrated in FIG. 9, the indication member 422 is located in only a front portion of the light emitting surface 402 but is not located around the end portion of the optical fiber 401. Further, the indication member 422 is provided at a surface of the protecting member 410. The indication member 422 is provided with an arrow direction having a directionality shape so that the irradiation position and the irradiation direction may be simultaneously confirmed.

Figure 10:
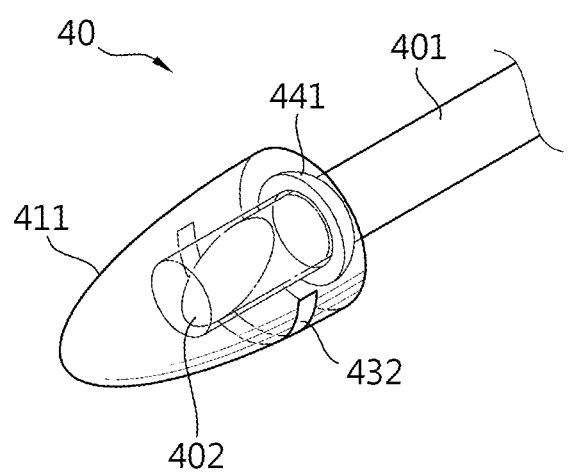
FIG. 10 is a perspective view illustrating a laser assembly according to a third embodiment of the present invention.

FIG. 10 is a perspective view illustrating a laser assembly according to a third embodiment of the present invention.

As shown in FIG. 10, the indication member 432 is located only around the optical fiber 401. The indication member 432 has a ring shape where one side is open and having directionality. Accordingly, if the shape of the indication member 432 is confirmed through X-ray, the irradiation position and the irradiation direction may be confirmed.

The above embodiments are illustrative purpose only for the present invention and an exemplary embodiment of the present invention not limited thereto. Since numerous variations and modifications will become apparent to those skilled in the art once the above disclosure is fully appreciated, the scope and spirit of the invention come within the scope of the appended claims and their equivalents.

What is claimed is:

1. A laser irradiation apparatus comprising:
   an optical fiber which transmits a laser and has an emitting end portion;
   a protecting member that covers the emitting end portion of the optical fiber; and
   a metal indication member arranged to indicate a position and a direction of the emitting end portion;
   wherein the emitting end portion comprises an inclined cut surface that reflects light out from the fiber in a direction transverse to an axis of the fiber, the indication member is located on a side of the optical fiber opposite to the direction in which the laser beam is transmitted, and at least a portion of the indication member overlaps the emitting end portion, so that the indication member indicates a position along the axis of the fiber and the direction in which the laser beam is transmitted,
   wherein the indication member comprises a front indication member located in a front portion of the light emitting surface in a longitudinal direction of the optical fiber and a lateral indication member located on a lateral side of the optical fiber, and the lateral indication member is longer than the front indication member.

2. The laser irradiation apparatus of claim 1, wherein the indication member is located in at least one of an inside and a surface of the protecting member.

3. The laser irradiation apparatus of claim 1, wherein the front indication member has a shape having directionality.

4. The laser irradiation apparatus of claim 1, wherein the lateral front marker has a shape having directionality.

* * * * *